United States Patent [19]
Cartwright

[11] 4,431,834
[45] Feb. 14, 1984

[54] HERBICIDAL BICYCLIC COMPOUNDS

[75] Inventor: David Cartwright, Woodley, England

[73] Assignee: Imperial Chemical Industries PLC, London, England

[21] Appl. No.: 363,227

[22] Filed: Mar. 29, 1982

[30] Foreign Application Priority Data

Apr. 16, 1981 [GB] United Kingdom ................. 8112109

[51] Int. Cl.$^3$ ............................................ C07C 69/76
[52] U.S. Cl. ....................................... 560/56; 560/10; 560/21; 560/45; 544/170; 546/205; 546/206; 562/427; 562/452; 564/162; 564/163; 564/166; 564/167; 564/168; 564/175; 564/180; 71/94; 71/95; 71/108; 71/114; 548/530

[58] Field of Search ....................... 560/56, 10, 21, 45; 544/170; 546/205, 206; 562/427, 452; 564/162, 163, 166, 167, 168, 175, 180; 260/326.2, 326.4; 71/94, 95, 108, 114

[56] References Cited

FOREIGN PATENT DOCUMENTS 14900 2/1980 European Pat. Off. .............. 560/21
2948095 11/1980 Fed. Rep. of Germany .

Primary Examiner—Paul J. Killos
Attorney, Agent, or Firm—Cushman, Darby & Cushman

[57] ABSTRACT

This invention relates to certain bicyclic derivatives which are indane and tetralin compounds and which have herbicidal properties, to processes for their preparation, to herbicidal compositions containing them and to a method of using them as herbicides.

7 Claims, No Drawings

HERBICIDAL BICYCLIC COMPOUNDS

The invention provides compounds of general formula (I):

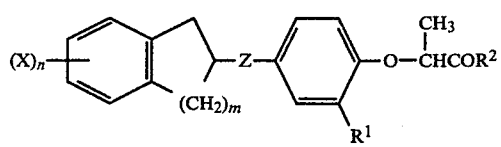

wherein X is hydrogen, halogen, trifluoromethyl, cyano, nitro, sulphonamido, $C_{1-4}$ alkyl, $C_{1-4}$ alkoxy, $C_{1-4}$ alkylthio, $C_{1-4}$ alkylsulphinyl or $C_{1-4}$ alkylsulphonyl; n is 1 or 2; m is 1 or 2; Z is —O—, —S—, —NH— or —N($CH_3$); $R^1$ is hydrogen or fluorine; and $R^2$ is hydroxy, $C_{1-6}$ alkoxy optionally substituted with hydroxy, carboxy, halogen or $C_{1-4}$ alkoxycarbonyl; cyclohexyloxy optionally substituted with halogen or $C_{1-4}$ alkyl; $C_{3-6}$ alkenyloxy; $C_{3-6}$ alkynyloxy; phenoxy optionally substituted with halogen or $C_{1-4}$ alkyl, benzyloxy optionally ring-substituted with halogen or $C_{1-4}$ alkyl; $C_{1-4}$ alkylsulphonamido; a group of general formula —$NR^3R^4$ wherein $R^3$ is hydrogen or $C_{1-4}$ alkyl and $R^4$ is $C_{1-4}$ alkyl optionally substituted with hydroxy or phenyl or $R^4$ is hydrogen, phenyl, chlorophenyl, $C_{1-4}$ alkoxy or a group of general formula —$NR^5R^6$ wherein $R^5$ is hydrogen or $C_{1-4}$ alkyl and $R^6$ is hydrogen, $C_{1-4}$ alkyl, phenyl or chlorophenyl, or the group —$NR^5R^6$ is pyrrolidine, piperidino or morpholino; or, in the case of a compound wherein $R^2$ comprises an acidic group, a salt thereof.

The compounds of general formula (I) wherein m is 1 are indane derivatives and those wherein m is 2 are tetralin derivatives. The numbering system employed to denote the position of substituents is shown below:

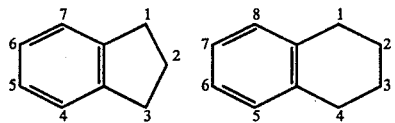

Examples of alkyl and alkoxy groups are methyl, ethyl, propyl (n- or i-propyl), butyl (n-, i-, sec- and t-butyl), methoxy and ethoxy. The halogen may be fluorine, chlorine, bromine or iodine. Examples of salts include metal salts eg alkali metal (for example sodium, potassium and lithium) salts and alkaline earth metal (for example calcium, strontium, and magnesium) salts, and ammonium salts eg salts formed with the ammonium cation or with a mono-, di-, tri- or tetra-substituted ammonium cation in which the substituents may be, for example, $C_{1-6}$ aliphatic radicals, e.g. $C_{1-6}$ alkyl.

The compounds of the invention contain an asymmetric carbon atom, and are therefore capable of existing in two optically isomeric forms. The present invention includes the dextro- and laevo-rotary isomers of each compound of the invention, and their mixtures in all proportions. The tetralin derivatives of the invention have an additional asymmetric carbon atom which is in the tetralin ring; the present invention also includes these isomers and their mixtures in all proportions.

Examples of the compounds of the invention are given in Table I:

TABLE 1

| COMPOUND NUMBER | (X)n | m | Z | $R^1$ | $R^2$ |
|---|---|---|---|---|---|
| 1 | H | 1 | —O— | H | n-Pro |
| 2 | H | 2 | —O— | H | n-Pro |
| 3 | 6-MeO— | 2 | —O— | H | n-Pro |
| 4 | 6-Cl— | 2 | —O— | H | n-Pro |
| 5 | 6-F | 2 | —O— | H | EtO |
| 6 | 6-Cl— | 2 | —O— | H | OH |
| 7 | 6-F | 2 | —O— | H | OH |
| 8 | 6-Me | 2 | —O— | H | n-PrO |
| *9 | 7-Cl | 2 | —O— | H | EtO |
| 10 | 5-Cl | 1 | —S— | H | EtO |
| 11 | H | 1 | —S— | H | EtO |

*The sample of this compound for which herbicide test results are given later in this specification comprised 80% by weight of the 7-chloro compound and 20% of its 5-chloro isomer. All the compounds in Table I were obtained in the form of viscous oils, for which no melting points can be quoted. However, the compounds were identified by their proton magnetic resonance spectra which were consistent with the structure assigned in each case.

Further examples of compounds falling within the scope of the invention are listed in Table 2 below:

TABLE 2

| COMPOUND NUMBER | (X)n | m | Z | $R^1$ | $R^2$ |
|---|---|---|---|---|---|
| 12 | 5-$CF_3$ | 1 | —O— | H | n-BuO— |
| 13 | 5-$CF_3$ | 1 | —O— | H | —OH |
| 14 | 6-$CF_3$ | 1 | —O— | H | n-BuO— |
| 15 | 6-$CF_3$ | 1 | —O— | H | —OH |
| 16 | 6-Cl | 2 | —O— | F | n-PrO— |
| 17 | 6-F | 2 | —O— | F | n-BuO— |

The compounds of the invention may be prepared by a variety of methods. One such method is illustrated in Scheme A below:

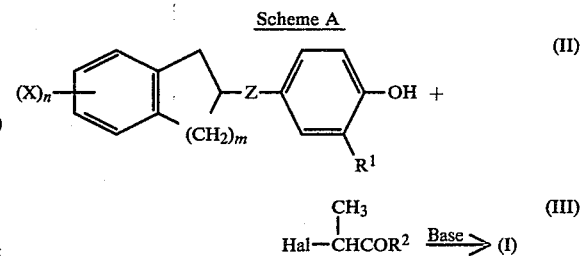

In Scheme A, the symbols X, m, n, Z and $R^1$ are as defined above and Hal is halogen (e.g. chlorine or bromine).

In Scheme A, the phenol derivative (II) is reacted with an alpha halogenopropionic acid derivative (III) to give the compound of the invention (I). The base may be for example an alkali metal carbonate, for example sodium or potassium carbonate, which is added to the reaction mixture in at least the stoichiometric amount. Alternatively, the sodium or potassium salt of the phenol derivative (II) may be pre-formed for example by treatment with sodium or potassium, or sodium or potassium hydroxide, and the salt then reacted with the alpha-halogeno compound (III) without further addition of base. The reaction is preferably carried out in a solvent or diluent for the reactants for example a ketone (e.g. methylethyl ketone or methyl isobutyl ketone) or dimethyl sulphoxide, dimethylacetamide, or tetrahydrofuran.

The compounds of formula (II) required for use in Scheme A may be prepared by a variety of processes. One such process comprises the reaction of a compound (IV) with a metal salt of a p-methoxyphenol as shown below:

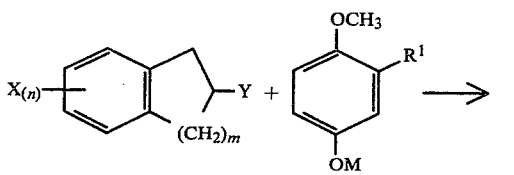
(IV)

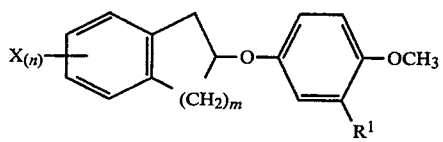
(VI)

In the above process, Y is halogen (e.g. chlorine or bromine) or alkanesulphonyloxy (e.g. methenesulphonyloxy). The metal salt M of the p-methoxyphenol is preferably an alkali metal salt (e.g. a sodium or potassium salt). The reaction is preferably carried out in a solvent or diluent (e.g. methylethyl ketone, tetrahydrofuran, dimethylsulphoxide, or dimethylacetamide, and is preferably accelerated by heating (e.g. to a temperature in the range 50°–150° C.). The product (VI) obtained by this reaction is then treated with a demethylating agent (e.g. pyridine hydrochloride or hydrogen bromide in acetic acid) by a standard procedure to give the required compound of formula (II). Alternatively, compounds of formula (II) may be prepared by reacting a hydroquinone derivative of the formula below:

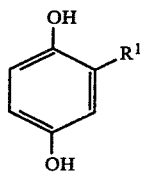

with a compound of formula (IV) in the presence of a base to give the compound of formula (II). The reaction is preferably carried out in a solvent or diluent for the reactants. Examples of solvents include aprotic solvents, for example dimethylformamide. The reaction is preferably accelerated by heating, for example to a temperature in the range 50°–150° C. The base used in the reaction may be, for example, an inorganic base, for example sodium or potassium carbonate. This reaction may be preferably used for compounds in which $R^1$ is hydrogen since its use for compounds in which $R^1$ is fluorine may lead to the formation of a mixture of isomers depending on whether the hydroxy group ortho or para to the fluorine atom reacts.

A further process for preparing compounds according to the invention is outlined in Scheme B below:

Scheme B

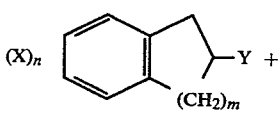
(IV)

-continued
Scheme B

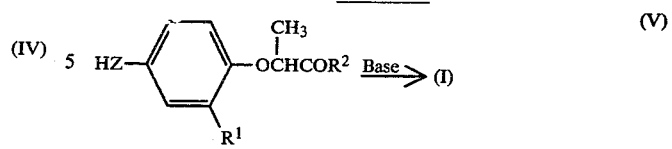
(V)

In Scheme B, the symbols have the meanings defined above. X, Y, Z, m, n, $R^1$ and $R^2$.

The compounds of the general formula (V) used in the process of Scheme B are either known or can be made by conventional methods. The reaction is preferably carried out in the presence of a solvent or diluent for the reactants, and is preferably accelerated by heating, for example to a temperature in the range 50°–150° C. Examples of solvents or diluents include lower alkyl ketones (e.g. methylethyl ketone). The base used in the reaction may be, for example, an inorganic base, for example sodium or potassium carbonate.

The compounds of formula (IV) required for the process of Scheme B are either known or may be prepared by conventional methods. Thus, for example, compounds of formula (IV) wherein m is 2 may be prepared by the reactions outlined in Scheme C below.

Scheme C

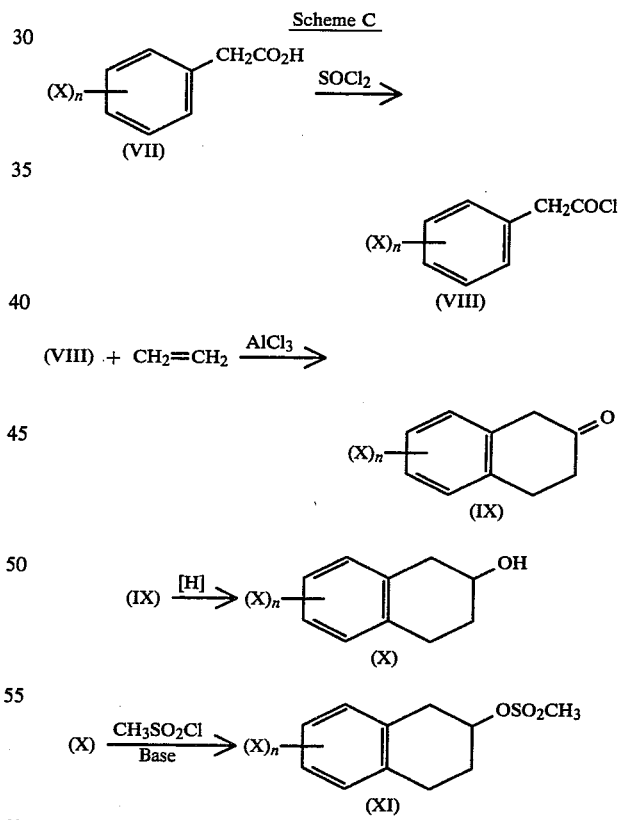

In Scheme C an appropriately substituted phenylacetic acid (VII) is reacted with a chlorinating agent (e.g. thionyl chloride) to convert it to the corresponding acid chloride (VIII). The reaction may be carried out at ambient temperatures or may be accelerated by heating. The acid chloride (VIII) is then reacted with gaseous ethylene in presence of anhydrous aluminium chloride to give the tetralone derivative (IX). Depending upon the position of the substituent(s) (X), mixtures of isomeric substituted tetralones may be produced; these may be separated if desired, by conventional methods. The tetralone (IX) is then reduced to the corresponding tetralinol (X); this may be done by conventional reducing methods (e.g. catalytic hydrogenation). In the laboratory it may be convenient to use sodium borohydride or lithium aluminium hydride as reducing agents. The tetralinol (X) is then converted to the methane sulphonyloxy derivative (XI) by reaction with methanesulphonyl chloride in presence of an acid acceptor. Conveniently, the acid acceptor is a tertiary amine (e.g. pyridine). Preferably the reaction is done in a solvent which may be for example an excess of pyridine above the amount required as acid acceptor.

Where a particular group $R^2$ is required to be present in the final product (I) according to the invention, the reactants for use in the above reaction schemes will usually be selected with the appropriate group $R^2$ already present. However, it may be desirable to transform a compound (I) having a particular group $R^2$ into another compound (I) having a different $R^2$ substituent. This may be done by conventional methods; thus, when $R^2$ is an —OH group, the compound may be converted to a salt by treatment with a base, according to standard procedures, or may be converted to an ester by reaction with an alcohol. Similarly, where $R^2$ is an alkoxy group, the compound may be converted to an amide by reaction with ammonia according to conventional methods.

The compounds of the invention are herbicides which are in general substantially more effective against grass species than against broad-leaved species of plants. They may be used to control unwanted grass species growing alone, or at suitable rates of application they may be used to control grass weeds growing among broad-leaved crop plants. Certain of the compounds of the invention are relatively less phytotoxic towards rice than they are towards other grasses, and these compounds have the potential to be used as selective herbicides in rice. Such compounds include, for example, compounds 8 and 9 of Table 1. The compounds may be either applied to the soil before the emergence of the unwanted grass species (preemergence application) or to the above-ground parts of growing plants (post-emergence application).

The invention also provides a process of inhibiting the growth of unwanted plants, particularly grass species, which comprising applying to the plants, or to the locus thereof, a herbicidally effective amount of a compound of formula (I) as hereinbefore defined.

The amount of the compound to be applied will depend upon a number of factors, for example the particular plant species whose growth is to be inhibited, but in general 0.025 to 5, preferably from 0.1 to 1, kilograms per hectare are used. The skilled worker in the art will readily be able to determine suitable amounts for use by means of standardised routine tests, without undue experimentation.

The compounds of the invention are preferably applied in the form of compositions, in which the active ingredient is mixed with a carrier comprising a solid or liquid diluent. Preferably the composition further comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth.

Solid compositions may also be in the form of dispersible powders or grains comprising in addition to the active ingredient, a wetting agent to facilitate the dispersion of the powder or grains in liquids. Such powders or grains may include fillers and suspending agents.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

The surface-active agents may be cationic, anionic or non-ionic surface-active agents. Suitable cationic agents are quaternary ammonium compounds, for example cetyltrimethyl ammonium bromide. Suitable anionic agents are soaps, salts of aliphatic mono-esters of sulphuric acid (for example sodium lauryl sulphate), and salts of sulphonated aromatic compounds (for example dodecylbenzenesulphonate, sodium, calcium and ammonium lignosulphonate, butylnaphthalene sulphonate, and a mixture of the sodium salts of diisopropyl- and triisopropylnaphthalenesulphonic acid). Suitable non-ionic agents are the condensation products of ethylene oxide with fatty alcohols such as oleyl alcohol and cetyl alcohol, or with alkyl phenols such as octylphenol, nonylphneol and octylcresol. Other non-ionic agents are the partial esters derived from long chain fatty acids and hexitol anhydrides, for example sorbitol mono-laurate, and the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment. In general concentrates may conveniently contain 10 to 85%, 25 to 60%, by weight of active ingredient. Dilute preparations ready for use may contain varying amounts of the active ingredient, depending upon the purpose for which they are to be used; however, dilute preparations suitable for many uses contain 0.01 to 10%, preferably 0.1 to 1%, by weight of the active ingredient.

The compounds of the invention can be used in association (for example in the form of a mixture) with another herbicide.

The other herbicide will generally be a herbicide having a complementary action, for example a herbicide active against broad-leaved weeds or a contact herbicide.

Examples of useful complementary herbicides are:

A. benzo-2,1,3-thiadiazin-4-one-2,2-dioxides such as 3-isopropylbenzo-2,1,3-thiadiazin-4-one-2,2-dioxide (bentazon);

B. hormone herbicides, particularly the phenoxy alkanoic acids such as 4-chloro-2-methylphenoxy acetic acid (MCPA), 2-(2,4-dichlorophenoxy)propionic acid (dichlorprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy)propionic acid (mecoprop), and their derivatives (e.g. salts, esters and amides);

C. 3-[4-(4-halophenoxy)phenyl]-1,1-dialkylureas such as 3-[4-(4-chlorophenoxy)phenyl]-1,1-dimethylurea (chloroxuron);

D. dinitrophenols and their derivatives (e.g. acetates) such as 2-methyl-4,6-dinitrophenol (DNOC), 2-t-butyl-4,6-dinitrophenol (dinoterb), 2-secbutyl-4,6-dinitrophenol (dinoseb) and its ester, dinoseb acetate;

E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin) and 4-methylsulphonyl-2,6-dinitro-N,N-dipropylaniline (nitralin);

F. phenylurea herbicides such as N'-(3,4-dichlorophenyl)N,N-dimethylurea (diuron) and N,N-dimethyl-N'-[3-(trifluoromethyl)phenyl]urea (flumeturon);

G. phenylcarbamoyloxyphenylcarbamates such as 3-[methoxycarbonylamino]phenyl (3-methylphenyl)-carbamate (phenmedipham) and 3-[etoxycarbonylamino]phenyl phenylcarbamate (desmedipham);

H. 2-phenylpyridazin-3-ones such as 5-amino-4-chloro-2-phenylpyridazin-3-one (pyrazon);

I. uracil herbicides such as 3-cyclohexyl-5,6-trimethyleneuracil (lenacil), 5-bromo-3-sec-butyl-6-methyluracil (bromacil) and 3-t-butyl-5-chloro-6-methyluracil terbacil);

J. triazine herbicides such as 2-chloro-4-ethylamino-6-(i-propylamino)-1,3,5-triazine (atrazine), 2-chloro-4,6-di (ethylamino)-1,3,5-triazine (simazine) and 2-azido-4-(i-propylamino)-6-methylthio-1,3,5-triazine (aziprotryne);

K. 1-alkoxy-1-alkyl-3-phenylurea herbicides such as 3-(3,4-dichlorophenyl)-1-methoxy-1-methylurea (linuron), 3-(4-chlorophenyl)-1-methoxy-1-methylurea (monolinuron) and 3-(4-bromo-4-chlorophenyl)-1-methoxy-1-methylurea (chlorobromuron).

L. thiolcarbamate herbicides such as S-propyl dipriopylthiocarbamate (vernolate);

M. 1,2,4-triazin-5-one herbicides such as 4-amino-4,5-dihydro-3-methyl-6-phenyl-1,2,4-triazine-5-one (metamitron) and 4-amino-6-t-butyl-4,5-dihydro-3-methylthio-1,3,4-triazin-5-one (metribuzin);

N. benzoic acid herbicides such as 2,3,6-trichlorobenzoic acid (2,3,6-TBA), 3,6-dichloro-2-methoxybenzoic acid (dicamba) and 3-amino-2,5-dichlorobenzoic acid (chloramben);

O. anilide herbicides such as N-butoxymethyl-α-chloro-2',6'-diethylacetanilide (butachlor), the corresponding N-methoxy compound (alachlor), the corresponding N-i-propyl compound (propachlor) and 3',4'-dichloro-propionanilide (propanil);

P. dihalobenzonitrile herbicides such as 2,6-dichlorobenzonitrile (dichlobenil), 3,5-dibromo-4-hydroxybenzonitrile (bromoxynil) and 3,5-diiodo-4-hydroxybenzonitrile (ioxynil).

Q. haloalkanoic herbicides such as 2,2-dichloropropionic acid (dalapon), trichloroacetic acid (TCA) and salts thereof;

R. diphenylether herbicides such as 4-nitrophenyl 2-nitro-4-trifluoromethylphenyl ether (fluorodifen), methyl 5-(2,4-dichlorophenoxy)-2-nitrobenzoate (bifenox), 2-nitro-5-(2-chloro-4-trifluoromethylphenoxy)-benzoic acid, 2-chloro-4-trifluoromethylphenyl 3-ethoxy-4-nitrophenyl ether and the compounds of European Patent Specification Publication No. 3416 (the disclosure of which Specification is incorporated herein by reference); and S. miscellaneous herbicides including N,N-dimethyldiphenylacetamide (diphenamid), N-(1-naphthyl)phthalamic acid (naptalam) and 3-amino-1,2,4-triazole. Examples of useful contact herbicides include:

T. bipyridylium herbicides such as those in which the active entity is the 1,1'-dimethyl-4,4'-dipyridylium ion (paraquat) and those in which the active entity is the 1,1'-ethylene-2,2'dipyridylium ion (diquat).

U. organoarsenical herbicides such as monosodium methanearsonate (MSMA); and

V. amino acid herbicides such as N-(phosphonomethyl)glycine (glyphosate) and its salts and esters.

The invention is illustrated by the following Examples wherein the temperatures are in degrees centigrade (°C.).

EXAMPLE 1

Stage 1

2-Indanol (1.34 g) in pyridine (5 ml) was stirred with cooling to 0° C. Methylsulphonyl chloride (1.38 g) was added dropwise while maintaining the temperature at 0°. The mixture was then allowed to warm to room temperature and was stirred for 0.5 hour. The mixture was then poured on to ice and immediately a white precipitate formed; the mixture was allowed to stand overnight. The precipitate was then filtered off, washed with water and air-dried to give 2-methylsulphonyloxyindane (1.9 g), m.p. 75°–77° C.

Stage 2

2-Methylsulphonyloxyindane (15.9 g) in methyl ethyl ketone (80 ml) was treated with potassium carbonate (15.53 g). The mixture was stirred and then n-propyl 2-(4-hydroxyphenoxy)propionate (16.8 g) in methyl ethyl ketone (20 ml) was added dropwise. The mixture was stirred at 90°–100° for 2.5 hours and was then poured into dilute hydrochloric acid. The mixture was extracted with ethyl acetate and the extract was washed thoroughly with water, dried and concentrated to an oil which semi-solidified on standing overnight. The oil was triturated with diethyl ether and petroleum ether. The mixture was filtered, and the filtrate concentrated to give an oil which was subjected to preparative thin layer chromatography on silica gel, eluting with chloroform/acetone/acetic acid (90:10:5), to give, as an oil, n-propyl 2-[4-(indan-2-yl-oxy)phenoxy]propionate (3.1 g).

EXAMPLE 2

Stage 1

2-tetralinol (0.86 g) in pyridine (5 ml) was stirred with cooling to 0°. Methylsulphonyl chloride (0.8 g) was added dropwise while maintaining the temperature at 0°. The mixture was then allowed to warm to room temperature and was stirred for 0.5 hour. The mixture was then poured on to ice and immediately a white precipitate formed; the mixture was allowed to stand overnight. The precipitate was then filtered off, washed with water and air-dried to give 2-methylsulphonyloxytetralin (0.72 g), m.p. 60°–62°.

Stage 2

2-Methylsulphonyloxytetralin (2.79 g) in methyl ethyl ketone (20 ml) was treated with potassium carbonate (2.6 g). The mixture was stirred and then n-propyl 2-(4-hydroxyphenoxy)propionate (2.77 g) in methyl ethyl ketone (10 ml) was added dropwise. The mixture was stirred at 90°-100° for 1 hour and was then left to stand overnight. The mixture was then stirred at 90°-100° for 2 hours and then poured into water. The mixture was extracted with ethyl acetate and the extracts were washed thoroughly with water, dried and concentrated to an oil. The mixture was subjected to preparative thin layer chromatography on silica gel eluting with chloroform/acetone/acetic acid (90:10:5), to give, as an oil, n-propyl 2-[4-(tetralin-2-yloxy)-phenoxy] propionate (0.47 g).

EXAMPLE 3

This Example illustrates a method of preparing compound no. 11 of Table 1.

A solution of 2-(p-methoxyphenylthio) indane (5 g) in dry dichloromethane (40 ml) was cooled to −70°. Boron tribromide (6 g) was added slowly with stirring at −70°. When addition was complete, the reaction mixture was kept at −70° for a further 10 minutes and then allowed to warm to room temperature. The mixture was left overnight and water (70 ml) then added slowly with stirring. The mixture was then poured into water (65 ml) and a further quantity (95 ml) of dichloromethane added, and the mixture agitated. The dichloromethane solution was separated and extracted with 2 molar sodium hydroxide. The cloudy extract was allowed to stand until it cleared and was then decanted from a residue. The solution was acidified with dilute hydrochloric acid and extracted with ether. The ether solution was washed with water, dried, and evaporated to give 2-(p-hydroxyphenylthio)indane.

The 2-(p-hydroxyphenylthio)indane so prepared (0.75 g) was heated and stirred under reflux with ethyl 2-bromopropionate (0.61 g) and anhydrous potassium carbonate (0.64 g) in dry methyl ethyl ketone (10 ml) for 6.5 hours. The mixture was then filtered and the filtrate evaporated under reduced pressure. The remaining brown oil was distilled (b.p. 200° C./0.5 Torr) to give compound no. 11 of Table 1 (0.66 g).

Following a similar procedure, ethyl 2[4(5-chloroindan-2-ylthio)phenoxy]propionate (compound no. 10 of Table 1) was prepared. The 5-chloro-2-p-methoxy-phenylthioindane required as starting material was prepared from 5-chloro-indane and p-methoxythiophenol, using the procedure described by Szmant and Breza, in the Journal of Organic Chemistry, 1980, volume 45, pp. 4902-4906; its identity was confirmed by examination of its proton magnetic resonance spectrum.

EXAMPLE 4

This Example illustrates a method of preparing compound no. 7 of Table 1, that is to say, 2-[4(6-fluorotetralin-2-yloxy)phenoxyl] propionic acid.

(a) p-Fluorophenylacetic acid (20 g) was stirred with thionyl chloride (30 ml) at room temperature for 5 hours. The excess of thionyl chloride was then removed under reduced pressure. The remaining oil was dissolved in toluene, and the toluene then removed under reduced pressure. The remaining oil was distilled (b.p. 41°-42°/0.1 mm) to give p-fluorophenylacetyl chloride (19.74 g).

(b) p-Fluorophenylacetyl chloride (17.25 g) in dichloromethane (100 ml) was added dropwise to aluminium chloride (26.7 g) suspended in dichloromethane (400 ml) maintained at −10° C. by cooling in a solid carbon dioxide/acetone bath. Ethylene gas was then passed through the mixture for 15 minutes while maintaining the temperature at −10° C. The mixture was then allowed to warm to room temperature and stirred for 3 hours. The mixture was then cooled to 5°-10° C. and ice and water (160 ml) added cautiously with stirring over a period of 45 minutes. The dichloromethane was then separated and washed successively with dilute hydrochloric acid, (150 ml×2), sodium bicarbonate solution (150 ml×2) and brine. The dichloromethane was then dried and evaporated. The residue was distilled to give 6-fluoro-2-tetralone (12.81 g) with a boiling range of 68°-76° C./0.05 Torr. The distillatte crystallised on standing.

(c) Sodium borohydride (1.67 g) was added in portions to a solution of 6-fluoro-2-tetralone (6.56 g) in dry ethanol (30 ml) with stirring, keeping the temperature below 25° C. The mixture was then stirred at room temperature for 3 hours. The mixture was then diluted with a little ethyl acetate and concentrated to an oily residue. Dilute sulphuric acid was added dropwise until effervescence no longer occurred. The mixture was extracted with ether and the extract washed, dried, and concentrated to give an oil. This was distilled (b.p. 75-77/0.1 Torr) to give 6-fluorotetralin-2-ol (5.31 g) containing a trace of the tetralone starting material.

(d) Methanesulphonyl chloride (6.62 g) was added dropwise to a solution of 6-fluoro-2-tetralinol (8 g) in dry pyridine (50 ml) cooled to below 5° C. When addition was complete, the reaction mixture was allowed to warm to room temperature and was stirred for 2 hours. The mixture was then poured into water, and the resulting mixture was extracted with ethyl acetate. The extract was washed with water, dried, and evaporated to give an oil. Trituration with a mixture of chloroform and petroleum ether (b.p. 30°-40° C.) gave an off-white solid identified as 6-fluoro-2-methanesulphonyloxy tetralin (8.31 g) with melting point of 52°-54° C.

(e) A solution of ethyl 2(4-hydroxyphenoxy)propionate (3.68 g) in dry methyl isobutyl ketone (15 ml) was added dropwise to a solution of 6-fluoro-2-methanesulphonyloxy tetralin (4.27 g) in dry methyl isobutyl ketone (40 ml) containing anhydrous potassium carbonate (4.5 g). The mixture was then stirred and heated to gentle reflux (ca. 125° C.) for 5 hours. The mixture was then poured into water and extracted with ethyl acetate. The extracts were washed with water, dried, and evaporated to give an oil. This was purified on thin-layer chromatographic plates using silica gel as the solid phase and a mixture of chloroform, cyclohexane, and methanol (50:50:10 by volume) as the eluent. Two main products were isolated; a mobile oil and a viscous oil. These were re-chromatographed using cyclohexane:-chloroform:methanol (45:15:10) as the eluent. The viscous oil proved to be the required product. The analytical results were as follows:

Found: C, 70.26; H, 6.26% $C_{21}H_{23}FO_4$ requires: C 70.37; H, 6.47%.

The product (Compound no. 5 of Table 1; 0.55 g) had a $n_D^{18} = 1.5448$ (f) The ethyl 2-[4(6-fluorotetralin-2-yloxy)-phenoxy]-propionate prepared according to paragraph (e) (0.2 g) was dissolved in isopropanol (4 ml) and a solution of sodium hydroxide (0.022 g in 1 ml) was added dropwise. The mixture was stirred at room temperature for 4 hours and then diluted with water, acidified with 2-molar hydrochloric acid, and concentrated to an oily residue under reduced pressure. The residue was extracted with ether. The extract was washed with water, dried and evaporated to give an oil (0.16 g) identified as compound no. 7 of Table 1 by examination of its proton magnetic resonance spectrum.

Following the procedure outlined in paragraphs (a) to (e) above, compounds 3, 4, 8 and 9 were prepared using the appropriately substituted phenylacetic acids as starting materials. Physical constants for the various intermediate products formed in these syntheses are given in the tables below:

| Acid chloride intermediates (structure VIII) | |
|---|---|
| Xn | Boiling point °C./Torr |
| 4-OCH$_3$ | 66–70/0.2 |
| 4-Cl | 56–58/0.15 |
| 4-CH$_3$ | 52–55/0.2 |
| 3-Cl | 60–66/0.1 |

| Tetralone intermediates (structure IX) | |
|---|---|
| Xn | Boiling point °C./Torr |
| 6-OCH$_3$ | 115–117/0.2 |
| 6-Cl | Solid |
| 6-CH$_3$ | 92–102/0.45 |
| *7-Cl | 140–150/0.5 |

| Tetralin-2-ol intermediates (structure X) | |
|---|---|
| Xn | Boiling point °C./Torr |
| 6-OCH$_3$ | 106–112/0.2 |
| 6-Cl | 140–148/0.4 |
| 6-CH$_3$ | 78–83/0.2 |
| *7-Cl | Purified by TLC |

| Methanesulphonate intermediates (structure XI) | |
|---|---|
| Xn | Boiling point °C./Torr |
| 6-OCH$_3$ | 73–75 |
| 6-Cl | — |
| 6-CH$_3$ | — |
| *7-Cl | 66–69 |

Notes
*These intermediates contained a proportion of the 5-chloro isomer.
1. In the case of the tetralin-2-ol intermediates, lithium anhydride in tetrahydrofuran was used as the reducing agent for the 6-chloro and 6-methyl compounds.
2. In the case of compounds 4, 8 and 9 a trace of caesium fluoride was added as a catalyst in the final reaction between the methane sulphonate intermediate and the ethyl 2-(4-hydroxyphenoxy)propionate.
3. Compound 6 was prepared by hydrolysis of compound 4 with sodium hydroxide following the procedure described in paragraph (f) above.

EXAMPLE 5

This Example illustrates the herbicidal properties of the compounds of the invention. Each compound was formulated for test by mixing it with 5 ml of an emulsion prepared by diluting 160 ml of a solution containing 21.1 grams per liter of Span 80 (a surface-active agent comprising sorbitan monolaurate) and 78.2 grams per liter of Tween 20 (a surface-active agent comprising a condensate of 20 moles of ethylene oxide with 1 mole of sorbitan monooleate) in methylcyclohexanone to 500 ml with water. The mixture so obtained was shaken with glass beads and diluted to 40 ml with water.

The spray composition so prepared was sprayed on to young pot plants (post-emergence test) of the species named at the end of Table 3 below, at a rate equivalent to 1000 liters per hectare. Damage to plants was assessed 14 days after spraying by comparison with untreated plants, on a scale of 0 to 5 where 0 is 0 to 20% damage and 5 is complete kill. In a test for pre-emergence herbicidal activity, seeds of the test species were placed on the surface of fibre trays of soil and were sprayed with the compositions at the rate of 1000 liters per hectare. The seeds were then covered with further soil. Three weeks after spraying, the seedlings in the sprayed fibres trays were compared with the seedlings in unsprayed control trays, the damage being assessed on the same scale of 0 to 5.

The results are given in Table 3 (a dash (—) means that no test was made).

TABLE 3

| COMPOUND NO | RATE OF APPLICATION kg/ha | PRE- OR POST-EMERGENCE APPLICATION | Sb | Rp | Ct | Sy | Mz | Ww | Rc | Sn | Ip | Am | Pi | Ca | Ga | Xs | Cs | Cv | Av | Dg | Al | St | Ec | Sh | Ag | Cn |
|---|---|---|---|---|---|---|---|---|---|---|---|---|---|---|---|---|---|---|---|---|---|---|---|---|---|---|
| 1 | 0.5 | Pre | 0 | 1 | 0 | 0 | 3 | 3 | 2 | 2 | 0 | | 0 | 0 | 0 | 0 | 0 | 0 | 2 | 1 | 3 | 2 | 4 | 1 | 2 | 0 |
| 1 | | Post | 0 | 0 | 0 | 0 | 4 | 3 | 0 | 0 | 0 | 0 | 0 | 0 | 0 | 1 | 1 | 0 | 2 | 1 | 0 | 2 | 5 | 1 | 1 | 0 |
| 1 | 2 | Pre | 0 | 1 | 0 | 0 | 4 | 4 | 5 | 0 | 0 | | 0 | 0 | 1 | 0 | 0 | 0 | 1 | 2 | 4 | 5 | 3 | 5 | 3 | 5 |
| 1 | | Post | 0 | 0 | 0 | 0 | 5 | 4 | 2 | 2 | 1 | | 0 | 0 | 0 | 0 | 0 | 1 | 4 | 1 | 3 | 4 | 5 | 1 | 3 | 0 |
| 2 | 0.5 | Pre | 0 | 0 | 0 | 0 | 3 | 3 | 1 | 0 | 0 | 0 | | 0 | 0 | 0 | 0 | 0 | 1 | 1 | 4 | 4 | 4 | 0 | 3 | 0 |
| 2 | | Post | 0 | 1 | 0 | 0 | 5 | 4 | 0 | 1 | 0 | | 0 | 0 | 0 | 0 | 0 | 0 | 2 | 2 | 2 | 4 | 5 | 3 | 4 | 0 |
| 2 | 2 | Pre | 0 | 0 | 0 | 0 | 4 | 5 | 3 | 1 | 0 | 0 | | 0 | 0 | 0 | 1 | 0 | 2 | 4 | 5 | 4 | 5 | 0 | 5 | 0 |
| 2 | | Post | 0 | 0 | 0 | 0 | 5 | 4 | 1 | 1 | 0 | | 0 | 0 | 0 | 0 | 0 | 0 | 3 | 3 | 3 | 4 | 5 | 1 | 3 | 0 |

Names of test plants in Table 3
Sb Sugar beet
Rp Rape
Ct Cotton
Sy Soya bean
Mz Maize
Ww Winter wheat
Rc Rice
Sn *Senecio vulgaris*
Ip *Ipomoea purpurea*
Am *Amaranthus retroflexus*
Pi *Polygonum aviculare*
Ca *Chenopodium album*
Ga *Galium aparine*
Xs *Xanthium spinosum*
Ab *Abutilon theophrasti*
Cs *Cassia obtusifolia*
Cv *Convolvulus aruensis*
Av *Avena fatua* (wild oats)
Dg *Digitaria sanguinalis*
Al *Alopecurus myosuroides*
St *Setaria viridis*
Ec *Echinochloa crus-galli*
Sh *Sorghum halepense*
Ag *Agropyron repens*
Cn *Cyperus rotundus*

EXAMPLE 6

This Example illustrates the herbicidal properties of further compounds according to the invention. The compounds were tested as described in Example 5. The results are given in Table 4 below.

TABLE 4

| COMPOUND NUMBER | RATE OF APPLICATION kg/ha | PRE- OR POST-EMERGENCE APPLICATION | Sb | Rp | Ct | Sy | Mz | Ww | Rc | Sn | Ip | Am | Pi | Ca | Ga | Xs | Ab | Cs | Av | Dg | Al | St | Ec | Sh | Ag | Cn |
|---|---|---|---|---|---|---|---|---|---|---|---|---|---|---|---|---|---|---|---|---|---|---|---|---|---|---|
| 3 | 2.0 | Pre | — | — | — | — | — | 1 | 1 | — | — | — | — | — | — | — | — | — | 0 | 1 | 2 | 0 | 0 | 0 | 2 | 0 |
|   |   | Post | — | — | — | — | — | 1 | 0 | — | — | — | — | — | — | — | — | — | 1 | 1 | 0 | 0 | 1 | 1 | 0 | 0 |
| 4 | 0.2 | Pre | — | 0 | 0 | 0 | 0 | 0 | 2 | — | 0 | — | — | 0 | 0 | 2 | 0 | 0 | 2 | 0 | 3 | 3 | 2 | 3 | 1 | 0 |
|   |   | Post | 0 | 0 | 0 | 0 | 4 | 2 | 3 | 1 | 0 | 0 | 0 | 0 | 0 | 0 | 0 | 0 | 3 | 3 | 5 | 3 | 4 | 4 | 3 | 0 |
| 5 | 0.2 | Pre | — | — | 0 | 0 | 3 | 3 | 0 | 0 | 0 | — | 0 | 0 | 0 | 0 | 0 | 0 | 4 | 5 | 5 | 5 | 5 | 4 | — | 0 |
|   |   | Post | 0 | 0 | 0 | 0 | 4 | 4 | 3 | 0 | 0 | 0 | 0 | 0 | 0 | 0 | 0 | 0 | 5 | 5 | 5 | 5 | 5 | 5 | — | 0 |
| 5 | 1.0 | Pre | — | — | 0 | 0 | 4 | 5 | 5 | 0 | 0 | 0 | 0 | 0 | 0 | 0 | 0 | 0 | 4 | 5 | 5 | 3 | 5 | 4 | 5 | 0 |
|   |   | Post | 0 | 0 | 0 | 0 | 5 | 3 | 4 | 0 | 0 | 0 | 0 | 0 | 0 | 0 | 0 | 0 | 3 | 5 | 5 | 4 | 5 | 5 | 5 | 0 |
| 6 | 1.0 | Pre | — | — | — | — | 2 | 4 | 4 | — | — | 0 | — | — | — | — | — | — | 3 | 5 | 4 | 5 | 5 | 4 | 4 | 0 |
|   |   | Post | — | — | — | — | 4 | 4 | 0 | — | — | — | — | — | — | — | — | — | 4 | 5 | 5 | 5 | 5 | 5 | — | 0 |
| 7 | 1.0 | Pre | 1 | 0 | 0 | 0 | 4 | 4 | 5 | 0 | 0 | 0 | 0 | 0 | 0 | 0 | 0 | 0 | 4 | 5 | 4 | 5 | 5 | 5 | — | 0 |
|   |   | Post | 1 | 1 | 0 | 0 | 5 | 4 | 3 | 1 | 0 | 0 | 0 | 0 | 0 | 0 | 0 | 0 | 0 | 5 | 2 | 0 | 0 | 0 | 4 | 2 |
| 8 | 0.2 | Pre | — | — | — | — | 0 | 0 | 0 | — | — | 0 | — | — | — | — | — | — | 0 | 2 | 2 | 3 | 3 | 1 | 0 | 0 |
|   |   | Post | — | — | — | — | 4 | 2 | 1 | — | — | — | — | — | — | — | — | — | 3 | 1 | 4 | 0 | 0 | 0 | 4 | 0 |
| 8 | 1.0 | Pre | — | — | — | — | 3 | 2 | 2 | — | — | — | — | — | — | — | — | — | 3 | 4 | 4 | 3 | 3 | 2 | 3 | 0 |
|   |   | Post | — | — | — | — | 5 | 2 | 2 | — | — | — | — | — | — | — | — | — | 2 | 3 | 4 | 1 | 0 | 0 | 0 | 0 |
| 9 | 0.2 | Pre | — | — | — | — | 0 | 0 | 0 | — | — | — | — | — | — | — | — | — | 0 | 0 | 1 | 4 | 2 | 2 | 0 | 2 |
|   |   | Post | — | — | — | — | 0 | 0 | 1 | — | — | — | — | — | — | — | — | — | 1 | 2 | 2 | 0 | 2 | 0 | 1 | 0 |
| 10 | 5.0 | Pre | — | — | — | — | — | 3 | — | — | — | — | — | — | — | — | — | — | — | — | — | — | — | — | — | — |
|   |   | Post | — | — | — | — | — | 0 | — | — | — | — | — | — | — | — | — | — | — | — | — | — | — | — | — | — |

I claim:
1. Compounds of formula (I)

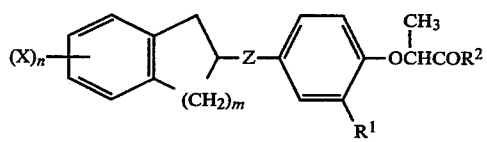

wherein X is hydrogen, halogen, trifluoromethyl, cyano, nitro, sulphonamido, $C_{1-4}$ alkyl, $C_{1-4}$ alkoxy, $C_{1-4}$ alkylthio, $C_{1-4}$ alkylsulphinyl or $C_{1-4}$ alkylsulphonyl; n is 1 or 2; m is 1 or 2; Z is —O—, —S—, —NH— or —N($CH_3$); $R^1$ is hydrogen or fluorine; and $R^2$ is hydroxy, $C_{1-6}$ alkoxy optionally substituted with hydroxy, carboxy, halogen or $C_{1-4}$ alkoxycarbonyl; cyclohexyloxy optionally substituted with halogen or $C_{1-4}$ alkyl; $C_{3-6}$ alkenyloxy; $C_{3-6}$ akynyloxy; phenoxy optionally substituted with halogen or $C_{1-4}$ alkyl; benzyloxy optionally ring-substituted with halogen or $C_{1-4}$ alkyl; $C_{1-4}$ alkylsulphonamido; a group of general formula —$NR^3R^4$ wherein $R^3$ is hydrogen or $C_{1-4}$ alkyl and $R^4$ is $C_{1-4}$ alkyl optionally substituted with hydroxy or phenyl or $R^4$ is hydrogen, phenyl, chlorophenyl, $C_{1-4}$ alkoxy or a group of general formula —$NR^5R^6$ wherein $R^5$ is hydrogen or $C_{1-4}$ alkyl and $R^6$ is hydrogen, $C_{1-4}$ alkyl, phenyl or chlorophenyl, or the group —$NR^5R^6$ is pyrrolidine, piperidino or morpholino; or, in the case of a compound wherein $R^2$ comprises an acidic group, a salt thereof.

2. Compounds as claimed in claim 1 wherein Z is oxygen.

3. Compounds as claimed in claim 1 or 2 wherein m is 2; X is halogen; $R^1$ is hydrogen; and $R^2$ is hydroxy or an alkoxy group of 1 to 6 carbon atoms.

4. A herbicidal composition, comprising a compound as defined in any of claims 1 to 3 in admixture with a carrier comprising a solid or liquid diluent, and optionally further comprising a surface-active agent.

5. A herbicidal composition, comprising a compound as defined in any of claims 1 to 3, in admixture with another herbicide.

6. A process of inhibiting the growth of unwanted plants, which comprises applying to the plants or to the locus thereof, a herbicidally effective amount of a compound of formula (I) as defined in any of claims 1 to 3.

7. A process of preparing a compound of the formula (I) as defined in claim 1, which comprises either
(a) reacting a substituted phenol of the formula (II)

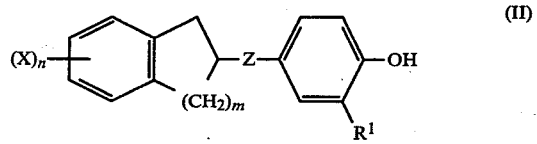

wherein X, m, n, Z and $R^1$ are as defined in claim 1 with an alphahalogeno propionic acid derivative (III)

in the presence of a base, or
(b) reacting a bicyclic derivative (IV)

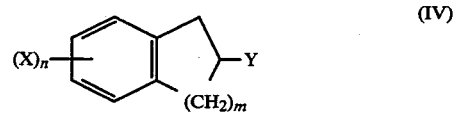

wherein X, m and n are as defined in claim 1 and Y is halogen or alkanesulphonyloxy with a substituted phenol of formula (V)

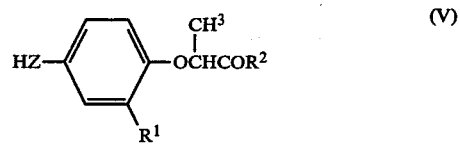

in the presence of a base, and recovering the compound of formula (I).

* * * * *